United States Patent
Miller et al.

[19]

[11] Patent Number: 6,133,990
[45] Date of Patent: Oct. 17, 2000

[54] METHOD FOR DETERMINING PRESENCE AND DISTRIBUTION OF CLOUDS

[75] Inventors: Theodore L. Miller, Penfield; Dennis A. Thompson, Scottsville, both of N.Y.; Steve Doerfel, Lawton, Okla.

[73] Assignee: Cambridge Management Advanced Systems Corp., Lawton, Okla.

[21] Appl. No.: 09/239,827

[22] Filed: Jan. 29, 1999

[51] Int. Cl.[7] .............................. G01C 3/08; G01N 21/00; G01W 1/00; G06F 19/00

[52] U.S. Cl. ..................... 356/4.01; 356/342; 356/5.01; 702/3

[58] Field of Search .................. 356/342, 4.01–5.15; 702/3

[56] References Cited

U.S. PATENT DOCUMENTS

| | | | |
|---|---|---|---|
| 3,650,627 | 3/1972 | Noxon . | |
| 4,259,592 | 3/1981 | Frunger et al. | 250/574 |
| 4,502,782 | 3/1985 | Werner et al. . | |
| 4,735,503 | 4/1988 | Werner et al. | 356/342 |
| 5,914,776 | 6/1999 | Streicher | 356/5.01 |

*Primary Examiner*—Stephen C. Buczinski
*Attorney, Agent, or Firm*—Venable; Laurence J. Marhoefer

[57] ABSTRACT

A method and process for the determination of presence and distribution of clouds is presented. The method involves the use of a sensor, such as laser ranger, for the collection of echo location measurement data from a three dimensional volume of the sky. The process involved in this invention utilizes the measurement data to evaluate and test for the presence of cloud banks. The process also utilizes the measurement data to quantitatively and qualitatively determine the cloud coverage amount and distribution. The preferred embodiment includes a laser ranger that samples the three dimensional volume at several azimuth-elevation angles through the application of a device capable of selecting azimuth-elevation angle values.

20 Claims, 11 Drawing Sheets

METHOD FOR DETERMINING PRESENCE AND DISTRIBUTION OF CLOUDS

BACKGROUND OF THE INVENTION

1. Field of Invention

This invention relates to an improved method, apparatus and related process for determining cloud cover conditions and cloud distribution in a region, and more particularly to a method and apparatus for making such a determination in the vicinity of an airport or airfield.

2. Description of Related Art

An ability to determine and report the distribution and amount of cloud coverage in the vicinity of an airport or airfield is of obvious importance to aircraft flight safety.

Clouds form where temperature and water content induce condensation of water vapor into droplets. In some instances, local heating causes air to rise. As it rises, the cooling process that occurs results in condensation and cloud formation. In other instances, wind distributions and the thermal structure of atmospheric weather systems cause boundaries with abrupt temperature changes. At these boundaries, clouds form due to both temperature and pressure effects. Many clouds assume a form referred to as a stratoform at these boundaries. That is, the clouds are naturally layered or stratified. Stratoform clouds and the somewhat less frequent convective cloud structure (tower cumulus, thunder cells, et cetera) are separate components of sky conditions. In determining and reporting sky conditions it is highly desirable to distinguish between these cloud types.

Cloud coverage measurements are frequently made by trained human observers or automatic instrumentation to determine sky conditions as described in Chapter 12—Sky Conditions, in the document entitled *Surface Weather Observing—METAR*, Department of Transportation, Federal Aviation Administration, document number 7900.5A, Washington, D.C., July 1996.

Human observers view a region around their location and determine, perhaps with the aid of the *WMO International Cloud Atlas*, such characteristics as ceiling, layers, sky cover classification, summation amount, and others. Human observers are limited in the quantity of observations they can make, and may suffer from significant variability from observer to observer.

Automatic instruments such as laser rangers (e.g. LIDAR) have also been used to measure cloud height. Such instruments collect data in only one, or relatively few, measurement directions. In addition, no attempt is made to determine the presence and/or movement of towering cloud structures. Consequently, such instruments provide incomplete reporting of cloud cover and cloud height.

SUMMARY OF THE INVENTION

The present invention utilizes an instrument capable of measuring sky conditions over a three dimensional volume, such as a hemisphere. The instrument is capable of pointing at any azimuth and elevation within the three dimensional volume. In operation, the instrument is pointed at a series of positions in the three dimensional volume and a measurement is made for each azimuth-elevation pair. The data obtained from a complete series of measurements is processed, alone or in comparison to previous data series, to provide cloud height, ceiling and cloud coverage information.

The invention provides a method for determining presence and distribution of clouds using a sensor capable of translating in azimuth and elevation, comprising: obtaining cloud presence data for at least two azimuth-elevation coordinates within a volume; processing said cloud presence data to produce a multi-dimensional representation of cloud distribution within said volume; and outputting said multi-dimensional representation of cloud distribution.

BRIEF DESCRIPTION OF THE DRAWINGS

FIG. 3A shows the pattern in a horizontal plane and FIG. 3B shows the pattern in a horizontal plane;

FIG. 4A shows the pattern in a horizontal plane and FIG. 4B shows the pattern in a horizontal plane;

DESCRIPTION OF PREFERRED EMBODIMENT

Figure 1:
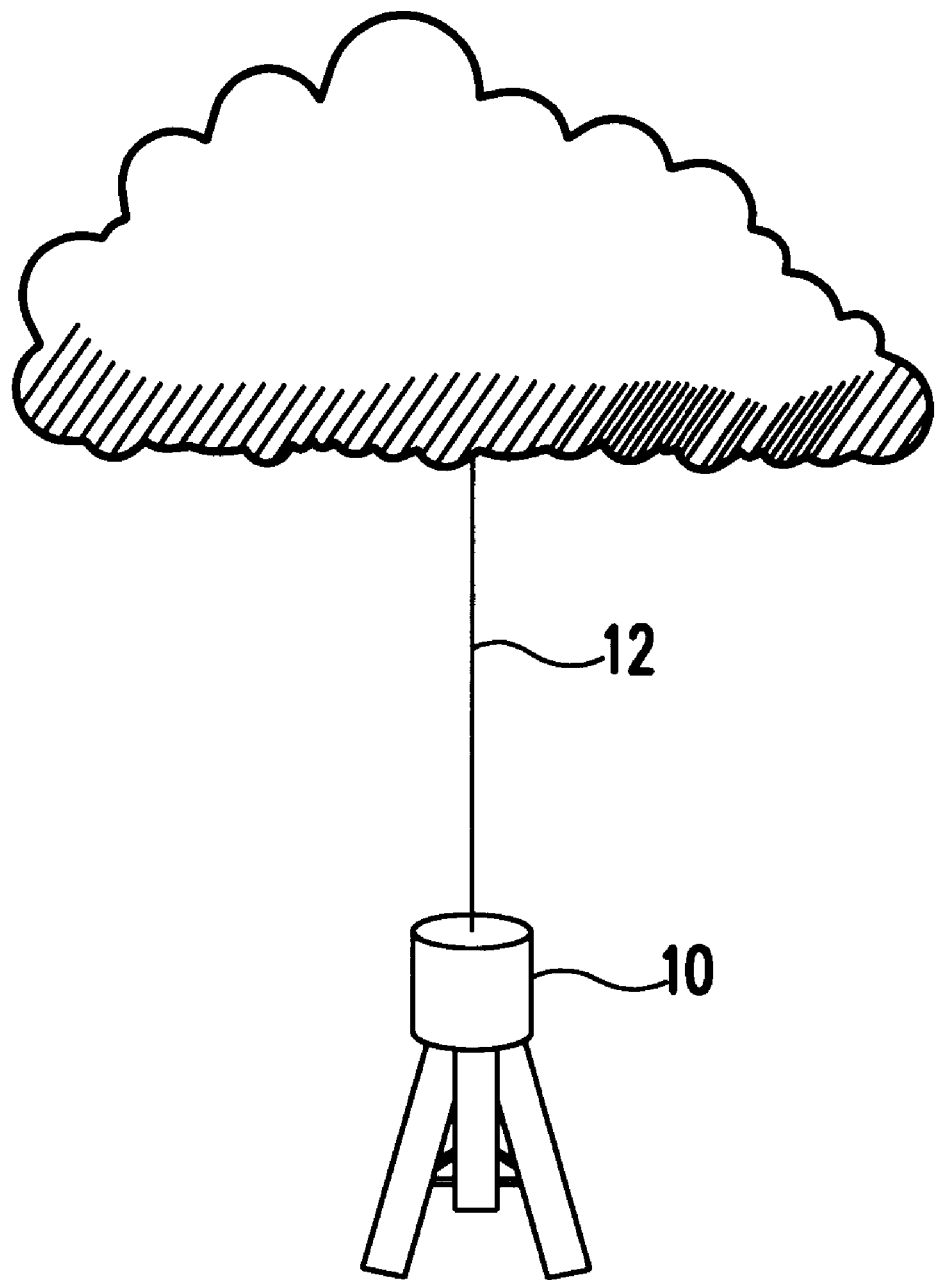
FIG. 1 shows an automatic instrument, called a ceilometer, for determining sky conditions.

Automatic instruments to measure sky conditions typically gather data in only one or a very few directions. For example, the most common type of these instruments are called ceilometers, as shown in FIG. 1, which measure sky conditions in a zenith direction (12) only. A ceilometer (10) has a limited field of view over which it can make measurements, and hence relies on movement of the clouds to obtain information about the sky conditions in a limited volume. Data gathered by such instruments are limited by the direction and speed of the cloud movement, and the length of time measurements are made.

Figure 2:
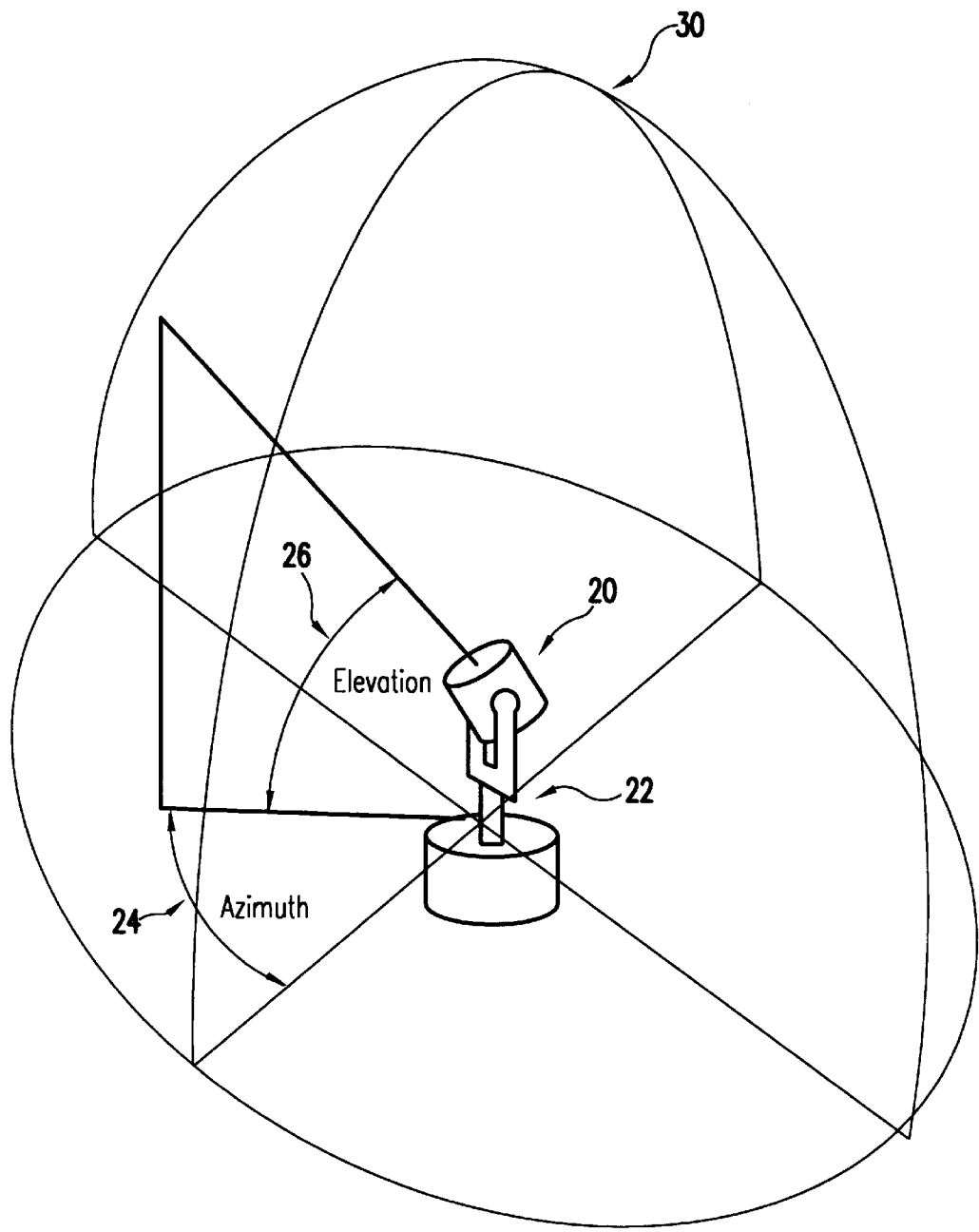
FIG. 2 shows an instrument for determining sky conditions in a three dimensional volume.

The present invention utilizes an instrument or sensor (20) capable of measuring sky conditions over a three dimensional volume (30). The sensor (20) can make a measurement over a small field of view. To gather data over a larger volume, this invention's sensor (20) is capable of pointing at any azimuth (24) and elevation (26) within the three dimensional volume (30). As shown in FIG. 2, the sensor (20) includes a steering mechanism (22) which can steer the field of view of the sensor (20) through a large volume. The steering mechanism (22) may include a gimbal, or other steering means such as a series of deflector mirrors. One embodiment of the present invention includes a two-axis gimbal mechanism which can steer or point the sensor (20) at any azimuth (24) and elevation angle (26). Yet another method of steering the sensor (20) is to provide an array of detectors which each measure a different portion of the three dimensional volume (30) around the instrument.

The shape of the three dimensional volume (30) may be an approximate hemisphere, or the volume may be some other shape such as a sector, a strip, a hyper-hemisphere or have a random shape.

In operation, the sensor (20) is pointed at a series of positions called a measurement pattern in the three dimensional volume (30), and a measurement is made for each desired azimuth (24)–elevation (26) pair in the measurement pattern. The data obtained from a complete series of measurements is processed, alone or in comparison to previous data series, to provide cloud height, ceiling and cloud coverage information.

The design of the measurement pattern, or sampling scheme, is important to the quality of the measurement data obtained. Enough data must be gathered to infer cloud coverage detail, and the selected measurement pattern should exhibit reasonably uniform sampling, relative ease of control, and the data set must be collected within a reasonable time. The time between the collection of the first piece of data in one data set and the first piece of data in a succeeding data set is called the data update rate. In one embodiment, the data update rate is approximately 10 minutes or less, while other embodiments may use other data update rates. It is even possible to have variable data update rates, depending on how fast the sky conditions are changing.

There are a number of alternative designs for the measurement pattern or sampling scheme. Two possible designs include equal angular increment measurement pattern (see FIG. 3), and equal spatial measurement pattern in a horizontal plane (see FIG. 4). Both of these sampling scheme geometries are referenced to a plane (40) parallel to and above the sensor plane (42). The sampling scheme or measurement pattern may also have to be adjusted to avoid possible obstructions and local geographic features, resulting in a three-dimensional volume (30) that only approximates a hemispherical shape.

Figure 3B:
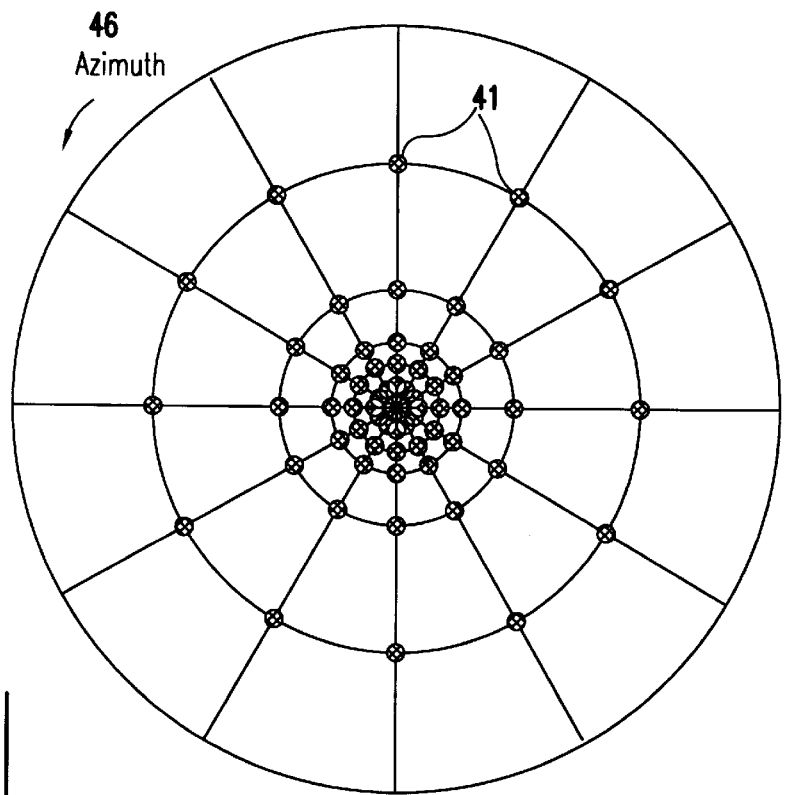
FIGS. 3A and 3B show a measurement pattern assuming equal angle increments.
Figure 3A:
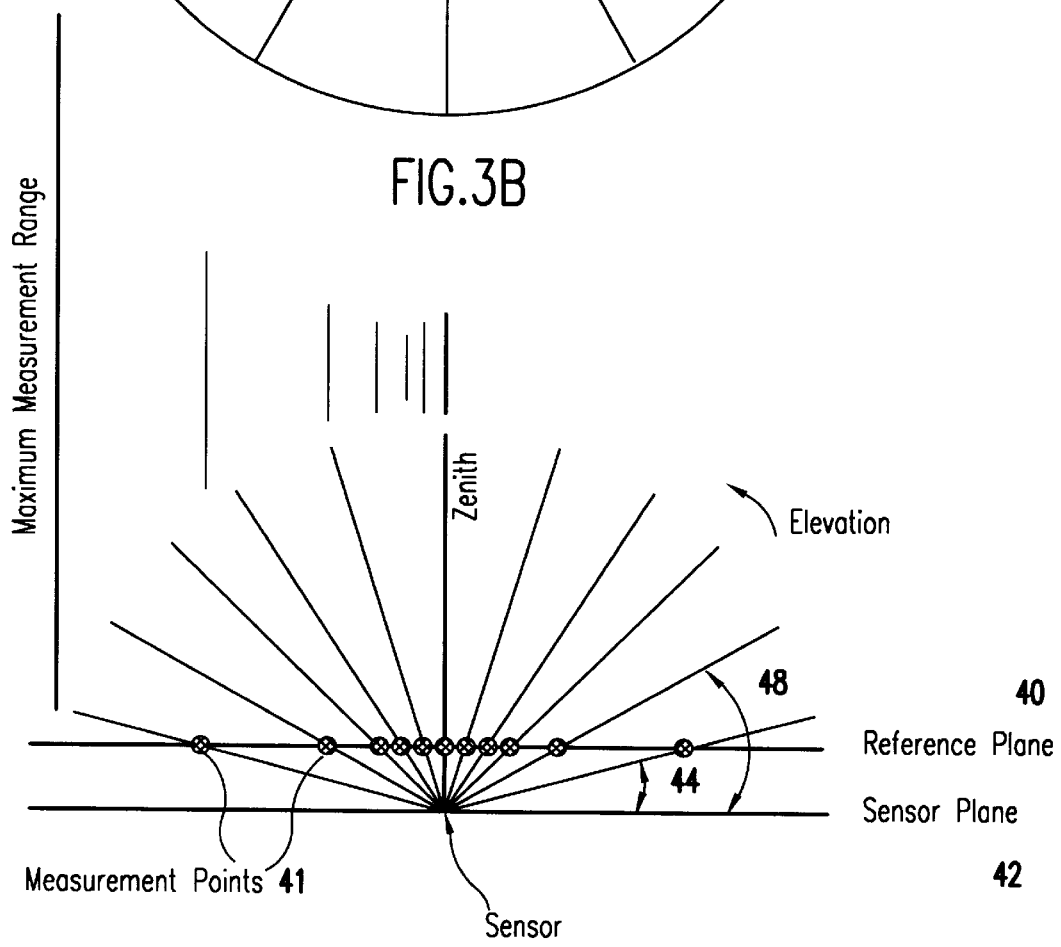

An equal angular increment measurement pattern is shown in FIG. 3. In this measurement pattern, a first elevation angle (44) is selected that is not significantly obscured by obstructions or geographic features. The sensor (20) starts at the first elevation angle (44) and moves through a series of selected azimuth angles (46). At selected azimuth-elevation positions, the sensor (20) makes a measurement (41). When all measurements are made for the first elevation (44), the elevation angle is incremented and the sensor (20) again moves through a series of selected azimuth angles. Again, measurements (41) are made at selected azimuth-elevation locations. When all measurements (41) are made for the second elevation (48), the elevation angle is again incremented by the same amount as the first elevation increment, and the measurement process is repeated. This process continues until the full three dimensional volume (30) has been measured, where the elevation angular increments are approximately the same between each successive elevation angle. Notice that this measurement pattern may have constant azimuth angular increments (46) for each elevation angle, or it may utilize different azimuth angle increments for each elevation angle. Also, it is possible to begin measurements at any elevation and azimuth pair, and proceed in any logical pattern to acquire measurements at all grid points in the measurement pattern.

Figure 4B:
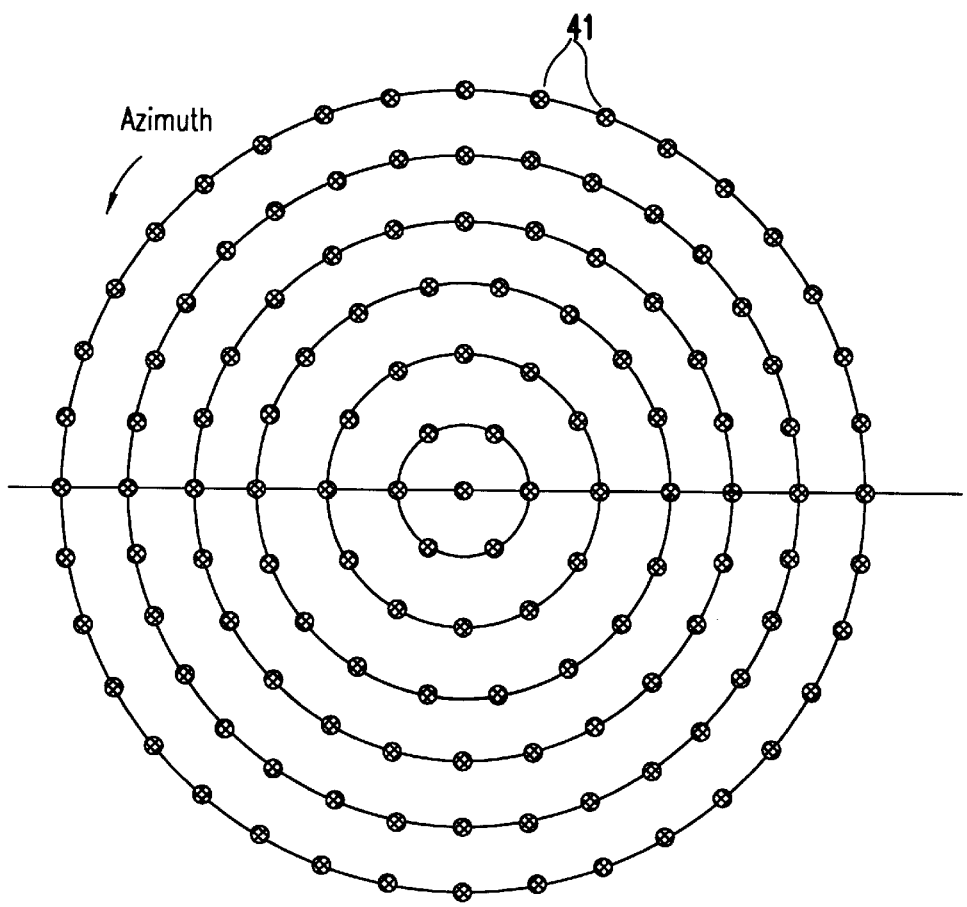
FIGS. 4A and 4B show a measurement pattern based approximately equally spaced points.
Figure 4A:
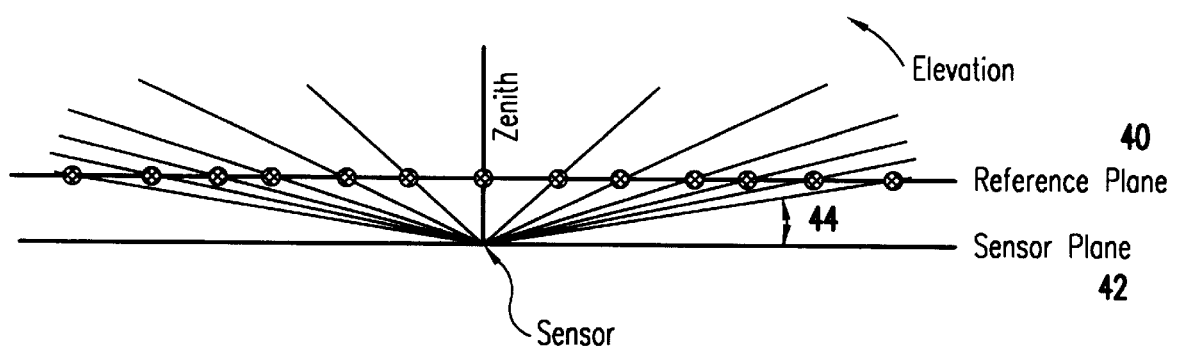

Another measurement pattern, shown in FIG. 4, provides equal spatial measurement areas in the plane containing the sensor. For this measurement pattern, a grid of measurement points (41) is determined in a reference plane (40) that is parallel to and above the plane (42) containing the sensor (FIG. 4A). Each grid point (41) is approximately the same distance from adjacent points. The instant example assumes a measurement pattern arranged in a series of concentric rings as shown in FIG. 4B, however it is clear that other patterns such as triangles, squares, hexagons, or other regular or irregular shapes may also be used. Starting at the location of the sensor, a unit distance is selected. This unit distance equals the radius from the zenith to the first ring of measurements. The radius of each successive ring is one unit distance greater than the previous ring. The largest diameter ring is limited by either the maximum range of the sensor, or a maximum value related to a minimum elevation angle which is not significantly obscured by obstructions or geographic features. The number of grid points (41) on each ring is approximately the circumference of the ring divided by the unit distance. Once the grid points (41) have been determined for each ring and zenith, the azimuth increment for each ring and the elevation increment between adjacent rings is determined so that the sensor (20) can be aimed at each grid point. Obviously, other methods may be used to select the grid points in the measurement pattern.

When using an equal spatial measurement pattern, the sensor (20) is first moved to that elevation angle (50) associated with the largest ring. A measurement is made and the azimuth of the sensor (20) is then incremented by the azimuth increment for that largest ring. This sequence of measurement and azimuth angle increment is repeated until all measurements (41) are made for the current ring.

The elevation of the sensor (20) is next adjusted to aim the sensor (20) at the next smaller ring, using the computed elevation increment between these adjacent rings. A measurement (41) is then made and the sensor's azimuth is incremented by the azimuth increment computed for the current ring. This sequence of measurement and azimuth increment continues until all measurements are made for the current ring. This process of incrementing elevation and azimuth continues until measurements are made for the complete measurement pattern. Again, it is possible to begin measurements (41) at any elevation and azimuth pair, and proceed in any logical pattern to acquire measurements at all grid points in the measurement pattern.

Figure 5:
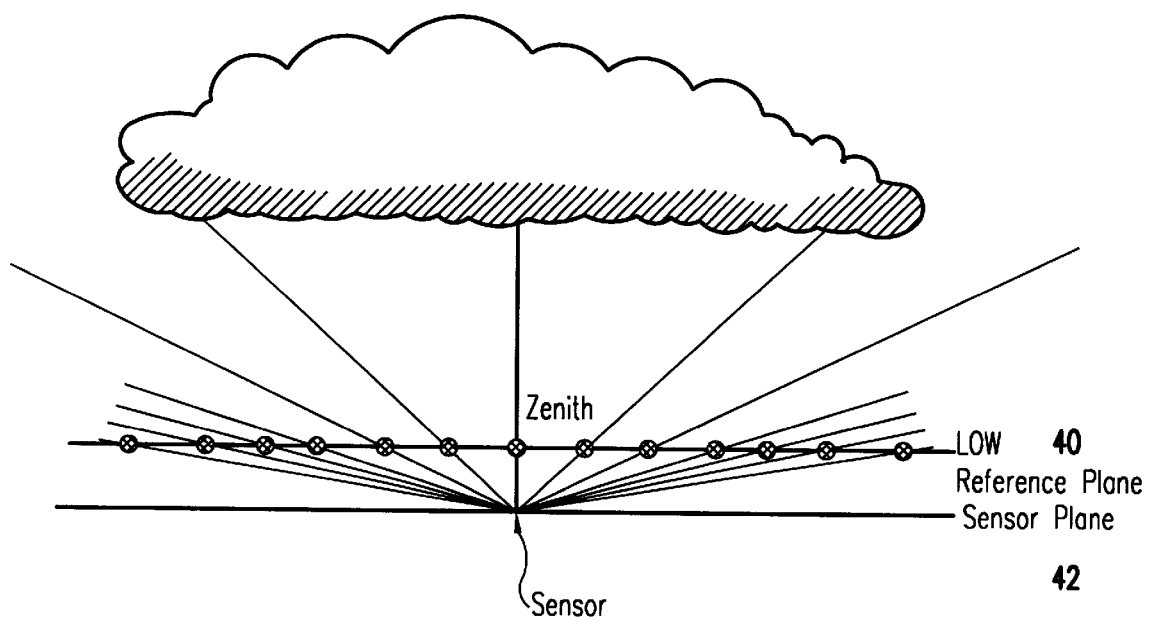
FIG. 5 shows high clouds with a measurement pattern based on low reference plane.
Figure 6:
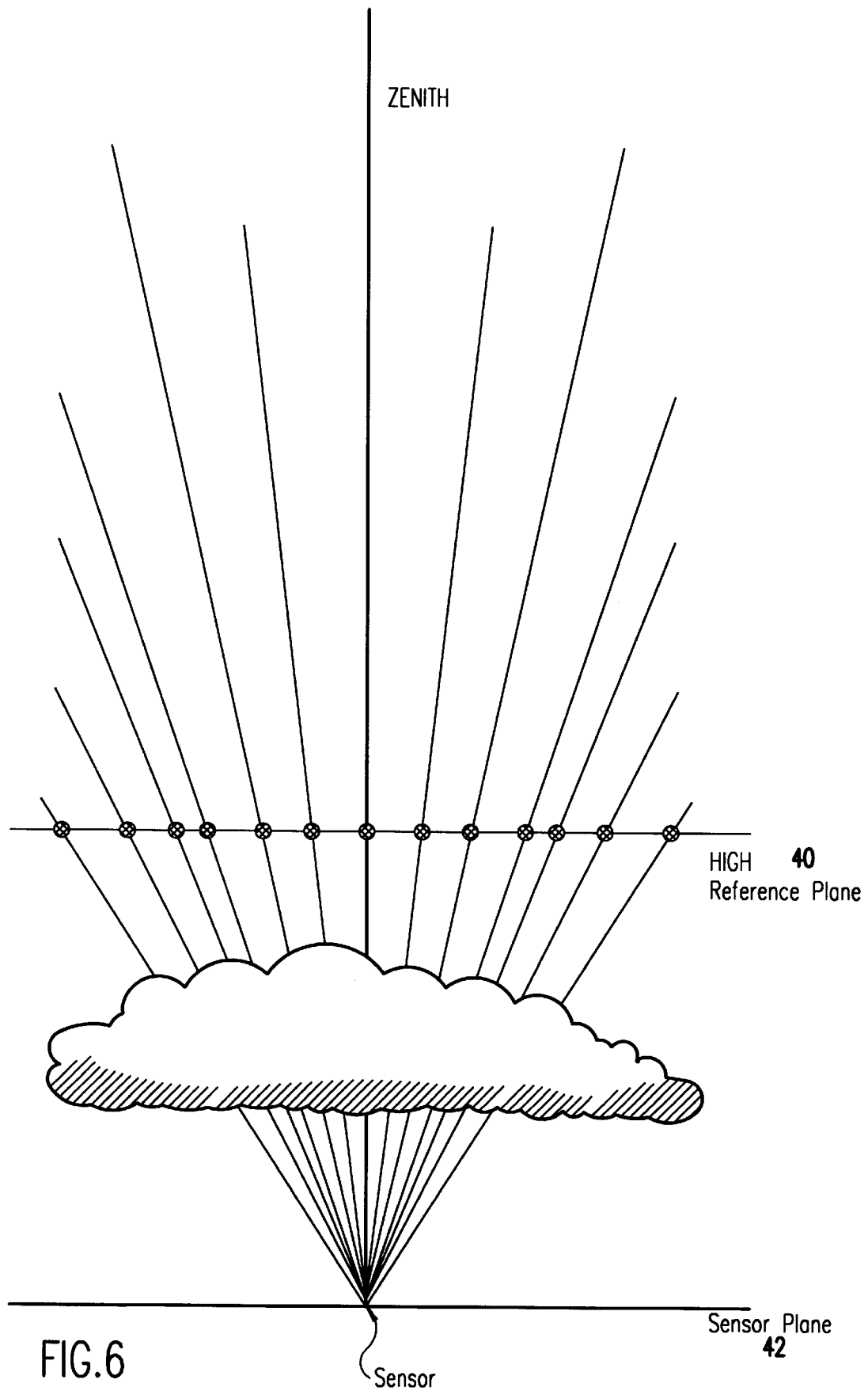
FIG. 6 shows low clouds with a measurement pattern based on a high reference plane.

The height of the reference plane (40) above the sensor plane (42) will determine the elevation (26) angles for a given measurement pattern. If a low reference plane (40) is used, then high altitude clouds may not be measured adequately (see FIG. 5). Similarly, if a high reference plane (40) is used, then sufficient data may not be collected for low clouds (see FIG. 6). Therefore, the sensor may adjust the reference plane (40) height to optimize the data collected.

Once the measurement data has been collected, it is processed to provide cloud distribution information. It is understood that measurement data may be processed as each data point is measured, or after all data in a measurement cycle have been collected. One embodiment of this data processing follows.

Figure 7:
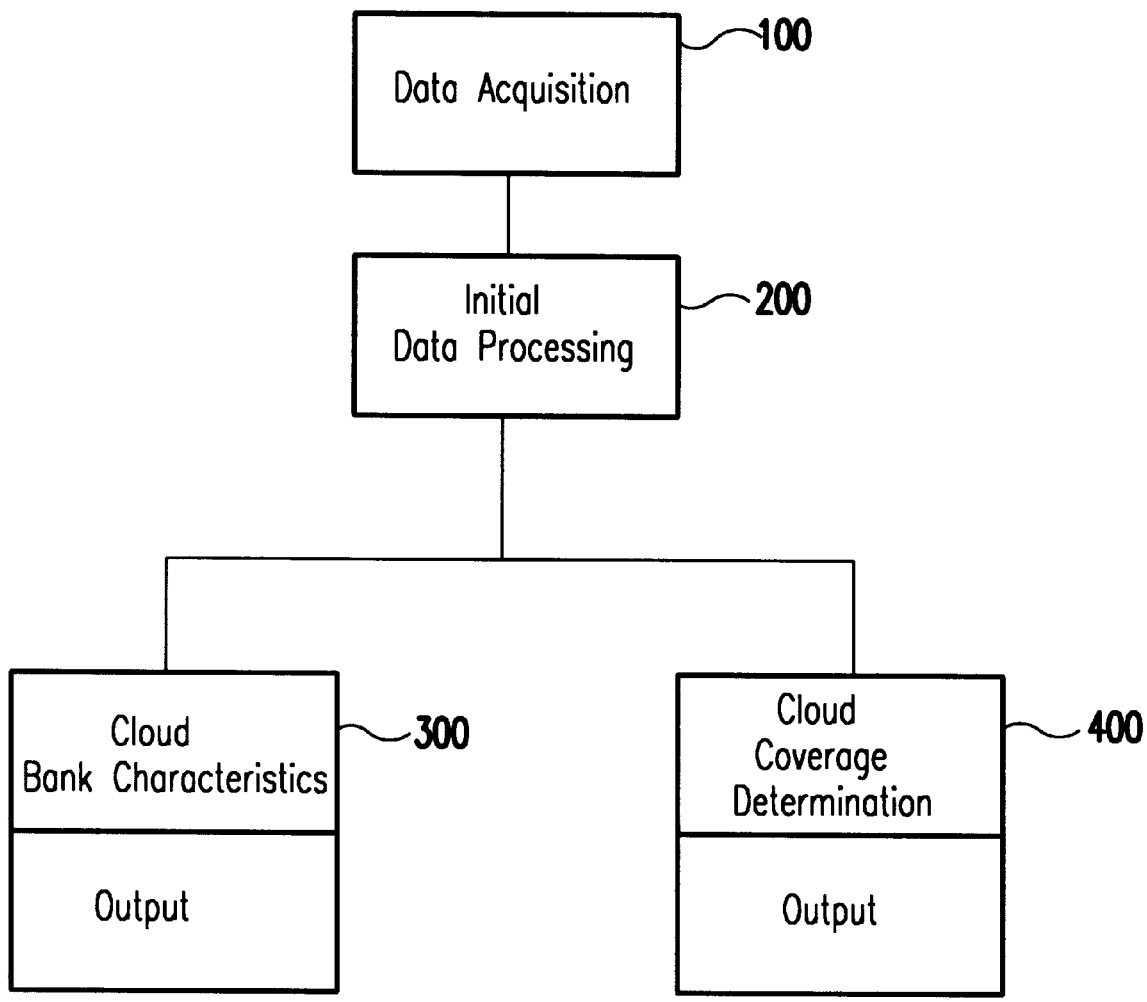
FIG. 7 shows the overall processing logic for the measurement data.

The process of determining the presence and distribution of clouds follows the guidelines presented in the FAA METAR. This process is next shown in FIG. 7, which has been divided into four major sections. These sections are:

the Data Acquisition (100) section is where a measurement pattern is selected, measurements are made, and calculations are performed on the measurement data;

the Initial Data Processing (200) section is where reference ranges and reference rings are selected, and cloud bank data and cloud coverage data are identified;

the Cloud Bank Characterization (300) section is where the cloud bank data is summarized, cloud bank structures are located and characterized, and the resulting information is output; and, the Cloud Coverage Determination (400) section is where the cloud coverage as a function of height is calculated based on cloud coverage data, and the resulting information is output.

Figure 8:
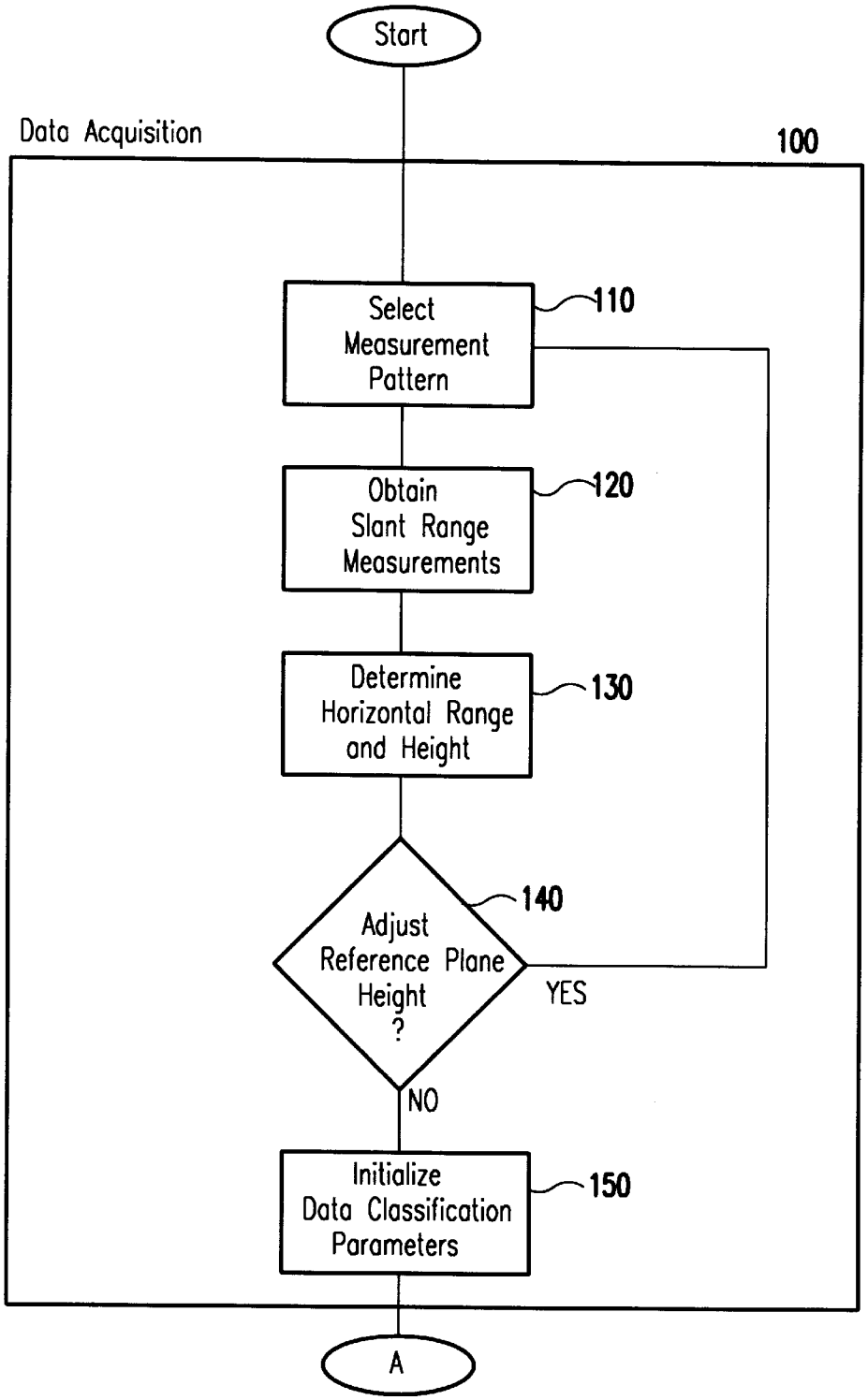
FIG. 8 shows the logic flow for data acquisition.

The first step in the data acquisition portion of the process of determining the presence and distribution of clouds (see FIG. 8) selects a measurement pattern (110) to be used to gather cloud presence data. Initially a default pattern is used that is based on a reference plane (40) which has, for example, a height of 12,000 feet. Optionally, other reference heights, such as 5,000 and 30,000 feet, may be used. As stated previously, the measurement pattern may consist of any combination of elevation and azimuth pairs, and proceed in any pattern or sequence to acquire measurements at all points in the measurement pattern. For the purpose of the remaining discussion, the measurement pattern shall be described as having equal spatial measurement areas.

The next step obtains measurements (120) of clouds, such as slant range data. The selected measurement pattern (110) is used. In one possible measurement pattern, the data may be collected for each azimuth from the lowest elevation angle to the highest elevation angle, or the reverse. Alternatively, data may be collected in any ordered or random sequence that addresses all points in the measurement pattern. Return signal confirmation and time-of-flight measurements permit the calculation of the slant range for each of the measurement orientations.

When the measurement produces a valid return signal, the horizontal range and height calculations are calculated (130) from simple geometrical relationships. If no valid return signal is received, the horizontal range and cloud height values for that measurement point are set to a large number. These values are used later in making cloud coverage determinations.

The next step (140) in the process checks to see if a different reference height should be selected for measurements based on the obtained data. This is done by evaluating the average cloud height in the current measurement data. If the average height of the current data is significantly different from the reference plane height, then another reference plane height may be selected that is closer to the average height of the data. The next measurement pattern (110) will then be based on this newly selected reference plane height.

The final part of the data acquisition portion (100) process is to initialize the data classification parameters (150).

Figure 9:
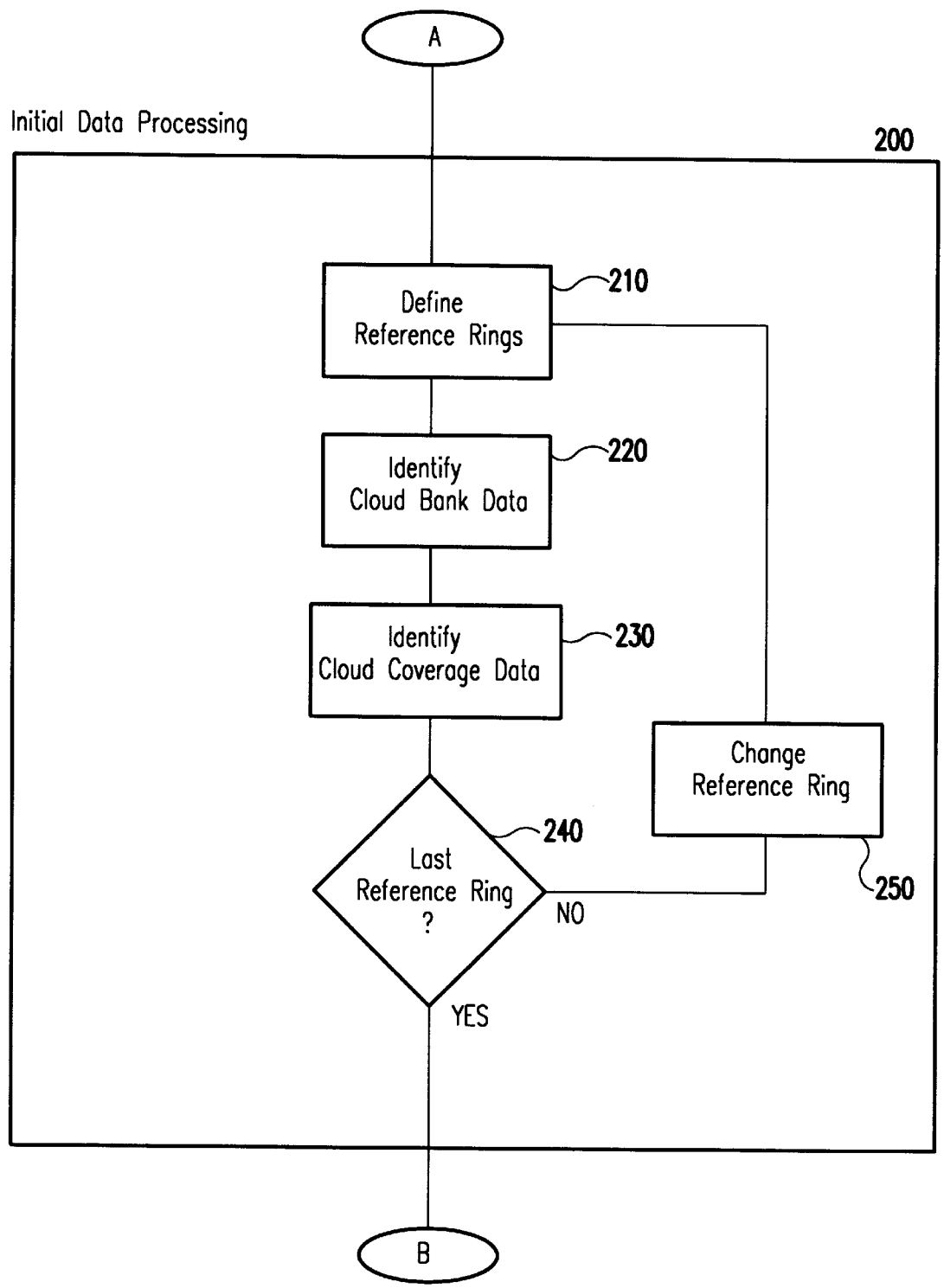
FIG. 9 shows the logic flow for the initial data processing.
Figure 10:
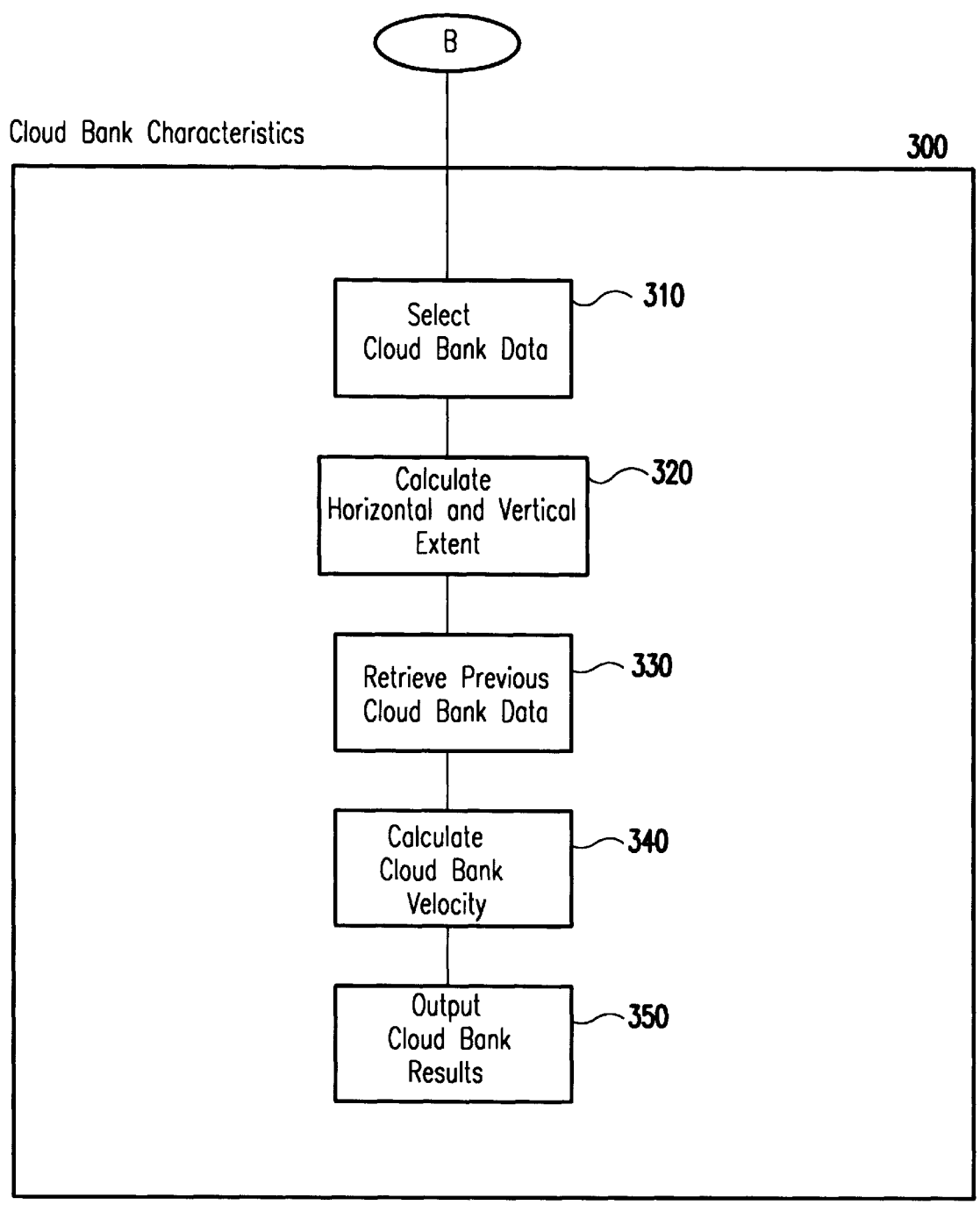
FIG. 10 shows the logic flow for cloud bank characteristics.
Figure 11:
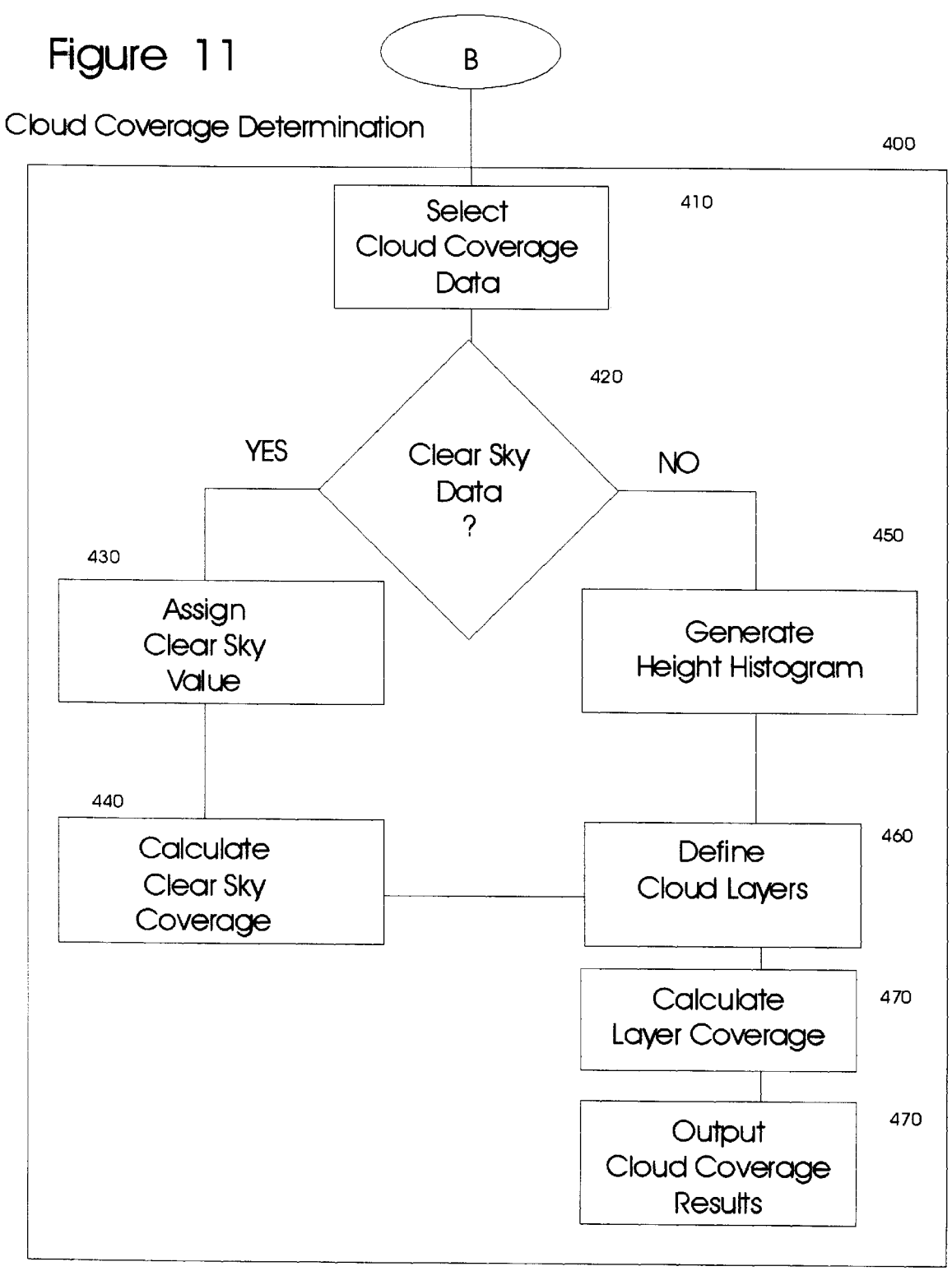
FIG. 11 shows the logic flow for cloud coverage determination.

The initial data processing step (200) classifies the measurement data obtained in the data acquisition step (100). See FIG. 9. All measurement data are classified into at least two sets, which may not be mutually exclusive. One set includes measurement data located on the sides of cloud banks. Another set of measurement data is used to determine cloud coverage.

One possible process for classifying the measurement data into sets is based on evaluating the relationship between horizontal range and height for spatially adjacent data. This relationship evaluation involves progressively searching through all of the measurement data in order to identify geometric structures such as cloud banks. One search method uses subsets of the measurement data called reference rings, which may be defined in many ways. One method for determining reference rings (210) defines a first reference ring that includes all measurement data for the lowest elevation angle and a first predetermined distance is defined as the corresponding data from that subset of data. These measurement data points are individually compared with measurement data from scans with successively higher elevation angles. Geometric criteria are used to specify those measurement data which are to be compared with the selected reference ring measurement data.

The comparisons continue until an appropriate correspondence between the reference ring range and the range for the measurement data point(s) under consideration no longer exists. This comparison process then continues by incrementing in the azimuth, and performing the same operations again, until all data points in the reference ring have been examined. A subsequent reference ring may then be defined as all measurement data with a different elevation angle and the comparison process is repeated. The comparison process continues in an iterative fashion until all the measurement data and the complete range of possible reference rings have been examined. Notice that the predetermined distances for each reference ring may be the same, or they may be different from each other.

While one method for determining reference rings has just been described, it is clear that many alternative methods may be used to form reference volumes within the measurement data. For example, generic reference rings, or reference volumes, might be used formed from nearest-neighbor measurement data. Other possible reference volumes could apply a weight to the measurement data within the reference volume based on the distance of the measurement data in the reference volume to the measurement data being evaluated.

The evaluation search process described earlier may also include an iterative component in order to adequately search all possible sets of adjacent data. Regardless of which combination of relationship evaluation, search process and reference rings (or volumes) is utilized, the classification process identifies those measurements in the measurement data set that show a change in height correlated with a small change in horizontal range. Measurement data selected by this classification process are identified as belonging to a cloud bank data set (220).

The next step in the initial data processing (200) sequence is the determination of those measurements that can be included in the cloud coverage data set (230). First, the cloud coverage data set includes all measurement data not belonging to the cloud bank data set. In addition, the cloud coverage data set may share some measurement data with the cloud bank data set.

The process of classifying the measurement data into cloud bank and cloud coverage data sets may involve a repetitive process that executes evaluations of the entire measurement data set multiple times (230, 240). In one embodiment, the evaluation is performed using measurement data in the first reference ring, then another reference ring is selected and the evaluation repeated. Obviously, many useful variations of this sequence could be utilized.

Following the initial data processing, the steps of determining cloud bank characteristics (300) and determining cloud coverage (400) may occur in a parallel or in a serial fashion, depending upon the physical features and capabilities of the data processing system being used. In the instant example embodiment, it is assumed that the processing of cloud bank measurement data occurs first, however alternative sequences are also possible.

The measurement data is checked to make certain that each measurement data point has been fully evaluated. Following this validation, the measurement data that characterizes cloud banks is evaluated to derive the spatial (lateral and vertical) extent of the one or several cloud banks that have been identified, if any (320). A distance test that identifies separate cloud banks is a part of this extent determination process. Following determination of extent (or size) of the cloud banks, an optional step may be implemented that retrieves one or more prior sets of cloud bank measurement data and associated cloud bank spatial extent results (330). This prior cloud bank information can then be directly compared to the current cloud bank information to determine the time history of the cloud banks. This cloud bank time history information can include speed and direction of movement of the cloud bank, and distance from the observing point or other significant features of local vicinity (340). Following these extend and history calculations, the cloud bank information and results are output (350).

The next segment of our preferred embodiment for processing measurement data is cloud coverage determination (400). First, the cloud coverage measurement data is selected from the full measurement data set (410).

Next, all cloud coverage measurement data are evaluated to identify measurement data which represent clear sky (420). In the preferred embodiment, invalid measurement data can occur when there is clear sky, or when there is fog or other atmospheric phenomena essentially at the location of the sensor (20). In the base of clear sky, there is no return signal and hence no measurement. In the case of local atmospheric phenomena, such as fog, the return signal occurs measures a very short range. In this short range case, the return signal can be large enough to damage the sensor and hence it is range gated out before it can be registered by the sensor (20). In the case of no return signal, the measurement is determined to represent clear sky, and any suitable number can be assigned as the measurement data (430). All azimuth-elevation pairs are considered in this portion of the process.

Following identification and assignment of clear sky measurement data points, a further test is carried out to identify the presence of fog or similar phenomena. This test is based on invalid return signal count statistics in which a threshold total count value is chosen. If the number of invalid return signal measurements exceeds the threshold total count value, a fog condition is declared (440). Differentiation between the all clear sky and fog cases is carried out using a distant hard target check point.

When all possible measurement data have been classified and all relevant measurement data values have been established, the preferred embodiment continues with the evaluation of valid cloud coverage measurement data. This valid could coverage measurement data is used to carry out a cloud layer determination process using a histogram or similar approach (450). A cloud layer determination process defines the mean height and cloud coverage (460). The process establishes a quatitative measure of the number of measurement data that can be assigned to any one histogram peak. The embodiment can include a threshold for declaring a layer cluster in the height histogram. Alternative techniques, for example the Delauna approach, may also be used.

Following identification of the layers and their mean heights, the layer count values, together with the clear sky coverage expressed in terms of number of measurement data with a suitable number value, are combined to calculate the layer coverage amount for each layer of clouds (470).

The final step in the cloud coverage determination process (400) is the output of relevant data such as, for example, mean layer heights, total number of clear sky measurements, observed coverage values derived from the layer coverage calculations and declaration of fog, if applicable (470). Data and results may be provided in a format consistent with the generation of METAR reports as defined in FAA METAR, document 7900.5A.

This invention and approach is consistent with FAA methodology. Other means may be used to define the coverage for other applications. In addition, this process incorporates the calculation of the area coverage provided by clear sky measurements.

PARTS LIST

10 ceilometer
12 zenith
20 sensor
22 steering mechanism
24 azimuth angle
26 elevation angle
30 three dimensional volume
40 reference plane
41 measurement points
42 sensor plane
44 first elevation angle
46 azimuth angle increments
48 second elevation angle
100–150 data acquisition process
200–250 initial data processing
300–350 cloud bank characteristics
400–470 cloud coverage determination

What is claimed is:

1. A method for determining presence and distribution of clouds using a sensor capable of translating in azimuth and elevation, comprising:

translating said sensor in azimuth and elevation to obtain cloud presence data for at least two azimuth-elevation coordinates within a volume;

processing said cloud presence data to produce a multi-dimensional representation of cloud distribution within said volume; and outputting said multi-dimensional representation of cloud distribution.

2. The method of claim 1 wherein said volume is approximately a hemisphere.

3. A method for determining presence and distribution of clouds using a sensor capable of translating in azimuth and elevation, comprising:

translating said sensor in azimuth and elevation to obtain cloud presence data for at least two azimuth-elevation coordinates in a predetermined pattern within a volume;

processing said cloud presence data to produce a multi-dimensional representation of cloud distribution within said volume; and outputting said multi-dimensional representation of cloud distribution.

4. The method of claim 3 wherein said predetermined pattern includes a constant azimuth angle increment for a given elevation.

5. The method of claim 3 wherein each elevation angle in said predetermined pattern has a different azimuth angle increment.

6. The method of claim 3 wherein said step of obtaining cloud presence data includes obtaining data in the zenith direction.

7. The method of claim 3 wherein said predetermined pattern includes at least three points each separated from the others by approximately a unit amount.

8. A method for determining presence and distribution of clouds using a sensor capable of translating in azimuth and elevation, comprising:

translating said sensor in azimuth and elevation to obtain cloud presence data for at least three measurements in a predetermined pattern within a volume;

processing said cloud presence data to produce a multi-dimensional representation of cloud distribution within said volume; and outputting said multi-dimensional representation of cloud distribution.

9. The method of claim 8 wherein said measurements are regularly spaced in a reference plane that lies above a plane that includes said sensor and that establishes elevation angles at which cloud presence data is obtained.

10. The method of claim 8 wherein said processing step applies weights to said cloud presence data to produce approximately equal measurement significance.

11. The method of claim 8 wherein said measurements are approximately equidistant from each other.

12. A process for determining presence and distribution of clouds, comprising:

acquiring cloud presence data;

processing said cloud presence data;

determining cloud bank results using said cloud presence data to detect a vertically extending edge of a cloud;

determining cloud coverage results using said cloud presence data;

outputting said cloud bank results; and outputting said cloud coverage results.

13. The process of claim 12 wherein said acquiring cloud presence data step includes:

selecting a measurement pattern;

obtaining cloud presence data using said measurement pattern;

determining cloud parameters using said cloud presence data; and determining if the height of a reference plane that lies above a plane that includes said sensor and that establishes elevation angles at which cloud presence data is obtained is acceptable; and changing said reference plane height if said current reference plane height is unacceptable.

14. The process of claim 12 wherein said processing of cloud presence data step includes:

defining a reference range and selecting a current reference ring around which cloud presence data has been obtained at spaced apart azimuth directions;

identifying current cloud bank data included in said cloud presence data;

identifying cloud coverage data included in said cloud presence data; and determining if said current reference ring is a final ring reference ring; and changing said current reference ring if said current reference ring is not the final reference ring.

15. The process of claim 14 wherein said determining cloud bank results step includes:

selecting said current cloud bank data;

determining horizontal cloud bank extent using said current cloud bank data; and determining vertical cloud bank extent using said current cloud bank data.

16. The process of claim 12 wherein said processing of cloud presence data step optionally includes:

retrieving previous cloud bank data; and determining temporal cloud bank characteristics using said current cloud bank data and said previous cloud bank data.

17. The process of claim 14 wherein said acquiring cloud presence data step includes:

selecting said cloud coverage data;

determining clear sky coverage data using said cloud coverage data;

determining cloud layer data using said cloud coverage data; and determining cloud layer coverage using said clear sky coverage data and said cloud layer data.

18. A process for determining presence and distribution of clouds, comprising:

acquiring cloud presence data, including selecting a measurement pattern, obtaining slant range measurements, determining horizontal range and height data using said slant range measurements, determining if the height of a current reference plane that lies above a plane that includes said sensor and that establishes elevation angles at which cloud presence data is obtained is acceptable, and changing said reference plane height if said current reference plane height is unacceptable;

processing said cloud presence data, including defining a reference range and selecting a reference ring around which cloud presence data has been obtained at spaced apart azimuth directions, identifying current cloud bank data, identifying current cloud coverage data, determining if a current reference ring is a final reference ring, and changing said current reference ring if said current reference ring is not the final reference ring;

determining cloud bank results using said current cloud bank data, including selecting said current cloud bank data, determining horizontal extent using said current cloud bank data, and determining vertical extent using said current cloud bank data;

determining cloud coverage results using said current cloud coverage data, including selecting current cloud coverage data, determining clear sky coverage data using said current cloud coverage data, determining cloud layer data using said current cloud coverage data, and determining cloud layer coverage using said clear sky coverage data and said cloud layer data;

outputting said cloud bank results; and outputting said cloud coverage results.

19. The process of claim 18 wherein said determining cloud bank results step optionally includes:

retrieving previous cloud bank data; and determining cloud bank characteristics using said current cloud bank data and said previous cloud bank data.

20. The process of claim 18 wherein said determining cloud coverage results step optionally includes:

retrieving previous cloud coverage data; and determining cloud coverage characteristics using said current cloud coverage data and said previous cloud coverage data.

* * * * *